United States Patent [19]

Alig et al.

[11] 4,272,630

[45] Jun. 9, 1981

[54] D-HOMOSTEROIDS

[76] Inventors: Leo Alig, 32 Liebrütistrasse, Kaiseraugst; Andor Fürst, 14 Magnolienpark, Basel; Marcel Müller, 10 Quellenweg, Frenkendorf, all of Switzerland; Ulrich Kerb, 7 Prinzregentenstrasse, Berlin, Fed. Rep. of Germany; Klaus Kieslich, 4 Strasse zum Löwen, Berlin, Fed. Rep. of Germany; Rudolf Wiechert, 8a Petzower Strasse, Berlin, Fed. Rep. of Germany

[21] Appl. No.: 111,424

[22] Filed: Jan. 11, 1980

[30] Foreign Application Priority Data

Jan. 24, 1979 [CH] Switzerland .............................. 707/79

[51] Int. Cl.³ .............................................. C07C 69/75

[52] U.S. Cl. ......................................... 560/6; 260/410; 424/303; 424/308; 424/311; 424/312

[58] Field of Search .............................. 560/6; 260/410

[56] References Cited

U.S. PATENT DOCUMENTS

| 4,029,692 | 6/1977 | Alig et al. ................................. 560/6 |
| 4,197,406 | 4/1980 | Alig .......................................... 560/6 |

FOREIGN PATENT DOCUMENTS

2122539  1/1972  France ......................................... 560/6

Primary Examiner—Robert Gerstl
Attorney, Agent, or Firm—Jon S. Saxe; Bernard S. Leon; James H. Callwood

[57] ABSTRACT

The present invention is directed to 3-oxo, 6,9-hydro or halo, 11-oxo or ($\alpha$—H,$\beta$—OH), 17a-alkanoyloxy, 17a$\beta$-carboxylate D-homosteroids which are useful as antiinflammatory agents.

7 Claims, No Drawings

D-HOMOSTEROIDS

The present invention is concerned with novel D-homosteroids.

SUMMARY OF THE INVENTION

The D-homosteroids provided by the present invention have the following general formula

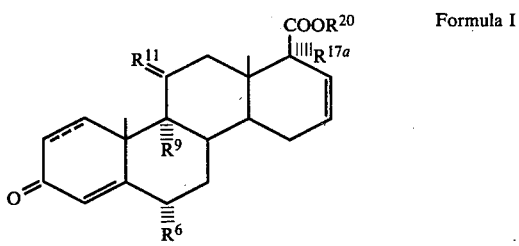

Formula I wherein $R^6$ is hydrogen, fluorine, chlorine or methyl; $R^9$ is hydrogen, fluorine, chlorine or bromine; $R^{11}$ is oxo or ($\alpha$-H, $\beta$-OH) when $R^9$ is hydrogen, or $R^{11}$ is oxo, ($\alpha$-H, $\beta$-OH), ($\alpha$-H, $\beta$-fluoro) or ($\alpha$H, $\beta$-chloro) when $R^9$ is fluorine, chlorine or bromine, with the proviso that, in the case of 9,11-dihalo compounds, the atomic number of the halogen in the 9-position is not less than the atomic number of the halogen in the 11-position; $R^{17a}$ is acyloxy and $R^{20}$ is lower alkyl or halo-(lower alkyl) and wherein the broken line in the 1,2-position denotes an optional carbon-carbon bond.

DETAILED DESCRIPTION OF THE INVENTION

An acyloxy group can be derived from a saturated or unsaturated aliphatic carboxylic acid, a cycloaliphatic carboxylic acid, an aralipathic carboxylic acid or an aromatic carboxylic acid preferably containing up to 15 carbon atoms. Examples of such acids are formic acid, acetic acid, pivalic acid, propionic acid, butyric acid, caproic acid, oenanthic acid, undecylenic acid, oleic acid, cyclopentylpropionic acid, cyclohexylpropionic acid, phenylacetic acid, salicyclic acid, acetylsalicyclic acid and benzoic acid. Especially-preferred acyloxy groups are alkanoyloxy groups containing from 1 to 7 carbon atoms. The lower alkyl groups can be straight-chain or branched-chain and can contain from 1 to 16 carbon atoms. Especially-preferred lower alkyl groups are those containing from 1 to 4 carbon atoms, especially methyl and ethyl. The lower alkyl moieties of the halo-(lower alkyl) groups have the same significance. The term "halo" includes fluoro, chloro, bromo and iodo unless expressly defined to the contrary. Examples of halo-(lower alkyl) groups are fluoromethyl, chloromethyl, bromomethyl, $\beta$-fluoroethyl, $\beta$-chloroethyl and $\beta$-bromoethyl.

In the case of 9,11-dihalo-D-homosteroids of formula I, the halogen atom in the 11-position should have a lower atomic number or the same atomic number as the halogen atom in the 9-position. In the case of D-homosteroids of formula I in which $R^9$ represents a hydrogen atom, $R^{11}$ can only represent an oxo or ($\alpha$—H, $\beta$—OH) group.

A preferred group of D-homosteroids of formula I comprises those in which $R^{11}$ represents a ($\alpha$-H, $\beta$-OH) group. Furthermore, those D-homosteroids of formula I in which $R^9$ is hydrogen or fluorine are preferred. D-homosteroids of formula I in which $R^{17a}$ is al-kanoyloxy containing from 1 to 7 carbon atoms and $R^{20}$ is methyl or fluoromethyl are also preferred.

Examples of D-homosteroids of formula I are:
17a-acetoxy-11$\beta$-hydroxy-3-oxo-D-homoandrosta-1,4,16-triene-17a$\beta$-carboxylic acid methyl ester,
11$\beta$-hydroxy-3-oxo-17a-propionyloxy-D-homoandrosta-1,4,16-triene-17a$\beta$-carboxylic acid chloromethyl ester,
11$\beta$-hydroxy-3-oxo-17a-propionyloxy-D-homoandrosta-1,4,16-triene-17a$\beta$-carboxylic acid fluoromethyl ester,
17a-acetoxy-3,11-dioxo-D-homoandrosta-1,4,16-triene-17a$\beta$-carboxylic acid methyl ester,
9-chloro-11$\beta$-fluoro-3-oxo-17a-propionyloxy-D-homoandrosta-1,4,16-triene-17a$\beta$-carboxylic acid chloromethyl ester,
9-bromo-11$\beta$-hydroxy-3-oxo-17a-propionyloxy-D-homoandrosta-1,4,16-triene-17a$\beta$-carboxylic acid chloromethyl ester,
11$\beta$-hydroxy-6$\alpha$-methyl-3-oxo-17a-propionyloxy-D-homoandrosta-1,4,16-triene-17a$\beta$-carboxylic acid methyl ester,
6$\alpha$-fluoro-11$\beta$-hydroxy-3-oxo-17a-propionyloxy-D-homoandrosta-1,4,16-triene-17a$\beta$-carboxylic acid fluoromethyl ester,
9-fluoro-11$\beta$-hydroxy-3-oxo-17a-propionyloxy-D-homoandrosta-1,4,16-triene-17a$\beta$-carboxylic acid chloromethyl ester,
17a-(o-acetoxy-benzoyloxy)-11$\beta$-hydroxy-3-oxo-D-homoandrosta-1,4,16-triene-17a$\beta$-carboxylic acid fluoromethyl ester,
17a-butyryloxy-11$\beta$-hydroxy-3-oxo-D-homoandrosta-1,4,16-triene-17a$\beta$-carboxylic acid ethyl ester,
9,11$\beta$-dichloro-3-oxo-17a-propionyloxy-D-homoandrosta-1,4,16-triene-17a$\beta$-carboxylic acid chloromethyl ester,
9-fluoro-11$\beta$-hydroxy-3-oxo-17a-propionyloxy-D-homoandrosta-1,4,16-triene-17a$\beta$-carboxylic acid methyl ester,
9-fluoro-11$\beta$-hydroxy-3-oxo-17a-propionyloxy-D-homoandrosta-1,4,16-triene-17a$\beta$-carboxylic acid fluoromethyl ester,
17a-acetoxy-6$\alpha$,9-difluoro-11$\beta$-hydroxy-3-oxo-D-homoandrosta-1,4,16-triene-17a$\beta$-carboxylic acid methyl ester,
17a-acetoxy-11$\beta$-hydroxy-3-oxo-D-homoandrosta-4,16-diene-17a$\beta$-carboxylic acid methyl ester,
11$\beta$-hydroxy-3-oxo-17a-propionyloxy-D-homoandrosta-4,16-diene-17a$\beta$-carboxylic acid chloromethyl ester,
11$\beta$-hydroxy-3-oxo-17a-propionyloxy-D-homoandrosta-4,16-diene-17a$\beta$-carboxylic acid fluoromethyl ester,
17a-acetoxy-3,11-dioxo-D-homoandrosta-4,16-diene-17a$\beta$-carboxylic acid methyl ester,
9-chloro-11$\beta$-fluoro-3-oxo-17a-propionyloxy-D-homoandrosta-4,16-diene-17a$\beta$-carboxylic acid chloromethyl ester,
9-bromo-11$\beta$-hydroxy-3-oxo-17a-propionyloxy-D-homoandrosta-4,16-diene-17a$\beta$-carboxylic acid chloromethyl ester,
11$\beta$-hydroxy-6$\alpha$-methyl-3-oxo-17a-propionyloxy-D-homoandrosta-4,16-diene-17a$\beta$-carboxylic acid methyl ester,
6$\alpha$-fluoro-11$\beta$-hydroxy-3-oxo-17a-propionyloxy-D-homoandrosta-4,16-diene-17a$\beta$-carboxylic acid fluoromethyl ester, 9-fluoro-11β-hydroxy-3-oxo-17a-propionyloxy-D-homoandrosta-4,16-diene-17aβ-carboxylic acid chloromethyl ester, 17a-(o-acetoxybenzoyloxy)-11β-hydroxy-3-oxo-D-homoandrosta-4,16-diene-17aβ-carboxylic acid fluoromethyl ester, and 17a-butyryloxy-11β-hydroxy-3-oxo-D-homoandrosta-4,16-diene-17aβ-carboxylic acid ethyl ester.

The present invention is also concerned with a process for the manufacture of the D-homosteroids of formula I. This process comprises (a) dehydrogenating a 1,2-saturated D-homosteroid of formula I in the 1,2-position, or (b) oxidizing the 3-hydroxy-$\Delta^5$ grouping in a D-homosteroid of the general formula

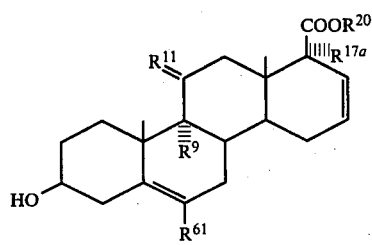

Formula II to the 3-keto-$\Delta^4$ grouping, or (c) fluorinating or chlorinating a D-homosteroid of the general formula

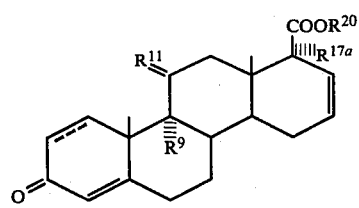

Formula III in the 6-position and, in another embodiment, isomerizing a 6β-isomer obtained to the 6α-isomer, or (d) methylating a D-homosteroid of the general formula

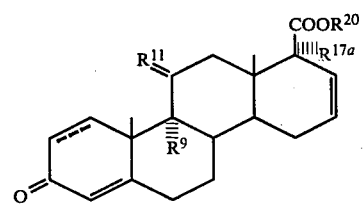

Formula III in the 6-position, or (e) subjecting a D-homosteroid of the general formula

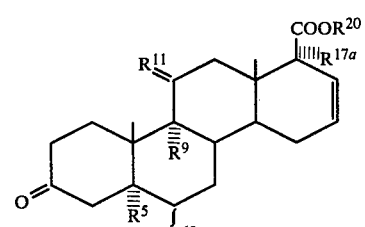

Formula IV to a HR$^5$-cleavage, or (f) adding chlorine, ClF, BrF, BrCl, hypochlorous acid or hypobromous acid to the 9,11-double bond of a D-homosteroid of the general formula

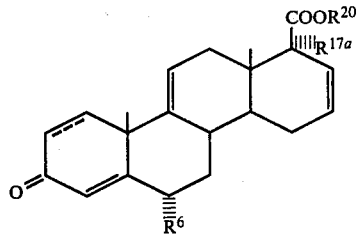

Formula V or (g) treating a D-homosteroid of the general formula

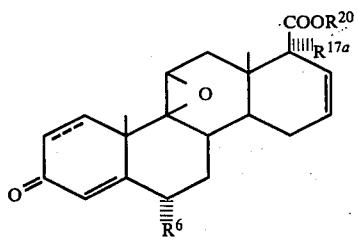

Formula VI with hydrogen fluoride, hydrogen chloride or hydrogen bromide, or (h) hydroxylating a D-homosteroid of the formula

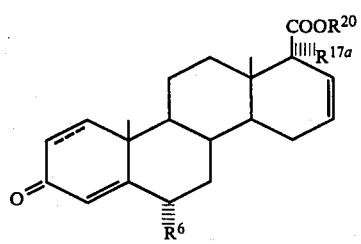

Formula VII in the 11-position by means of microorganisms or enzymes obtained therefrom, or (i) reducing the 11-keto group in a D-homosteroid of the general formula

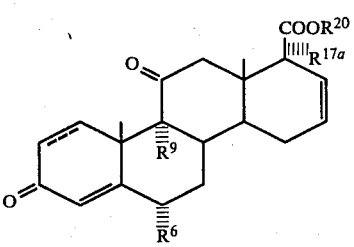

Formula VIII to the 11β-hydroxy group, or (j) oxidizing the 11-hydroxy group in a D-homosteroid of the general formula

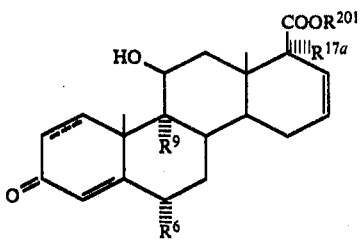

Formula IX to the keto group, or (k) acylating the 17aα-hydroxy group in a D-homosteroid of the general formula

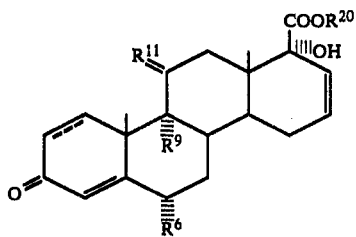

Formula X or (l) functionally modifying the group —COOR$^{201}$ in a D-homosteroid of the general formula

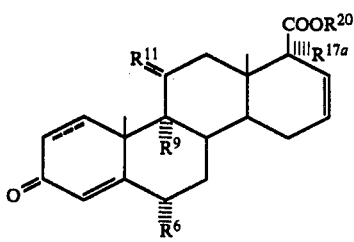

Formula XI or (m) hydrogenating the 1,2-double bond in a D-homosteroid of the general formula

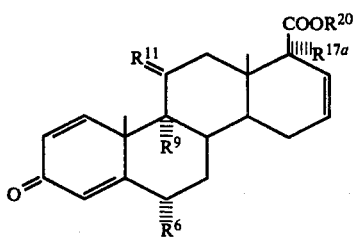

Formula XII wherein in the foregoing formulae R$^6$, R$^9$, R$^{11}$, R$^{17a}$ and R$^{20}$ and the broken line in the 1,2-position have the significance given earlier, R$^5$ is hydroxy or fluorine, chlorine or bromine, R$^{61}$ is hydrogen or methyl, R$^{62}$ is fluorine or chlorine or methyl and R$^{201}$ is hydrogen or R$^{20}$.

The 1,2-dehydrogenation of a D-homosteroid of formula I, in accordance with embodiment (a) of the process, can be carried out in a manner known per se; for example, in a microbiological manner or by means of dehydrogenating agents such as iodine pentoxide, periodic acid, selenium dioxide, 2,3-dichloro-5,6-dicyanobenzoquinone, chloranil or lead tetraacetate. Suitable microorganisms for the 1,2-dehydrogenation are, for example, Schizomycetes, especially those of the genera Arthrobacter (e.g. *A. simplex* ATCC 6946), Bacillus (e.g. *B. lentus* ATCC 13805 and *B. sphaericus* ATCC 7055), Pseudomonas (e.g. *P. aeruginosa* IFO 3505), Flavobacterium (e.g. *F. flavenscens* IFO 3058), Lactobacillus (e.g. *L. brevis* IFO 3345) and Nocardia (e.g. *N. opaca* ATCC 4276).

The oxidation of a D-homosteroid of formula II, in accordance with embodiment (b) of the process, can be carried out according to methods known per se; for example, according to the Oppenauer procedure using aluminium isopropylate or by means of oxidizing agents such as chromium trioxide (e.g. Jones' reagent), or according to the Pfitzner-Moffatt procedure using dimethyl sulphoxide/dicyclohexylcarbodiimide (the initially obtained Δ$^5$-3-ketone requiring subsequent isomerization to the Δ$^4$-3-ketone) or by means of pyridine/sulphur trioxide.

The fluorination or chlorination of a D-homosteroid of formula III in the 6-position, in accordance with embodiment (c) of the process, can be carried out in a manner known per se. A 6,7-saturated D-homosteroid of formula III can be fluorinated or chlorinated by reaction with a fluorinating or chlorinating agent such as a N-chloramide or imide (e.g. N-chlorosuccinimide) or with elemental chlorine [see J. Am. Chem. 72, 4534 (1950)]. This embodiment of the process is preferably carried out by converting a 6,7-saturated D-homosteroid of formula III into a 3-enol ester or 3-enol ether (e.g. the 3-enol acetate) and reacting the 3-enol ester or 3-enol ether with chlorine [see J. Am. Chem. Soc. 82, 1230 (1960)], with a N-chloroimide [see J. Am. Chem. Soc. 82, 1230 (1960); 77, 3827 (1955)] or with perchloryl fluoride [see J. Am. Chem. Soc. 81, 5259 (1959); Chem. and Ind. 1959, 1317]. Trifluoromethyl hypofluorite can also be used as the fluorinating agent.

Insofar as the previously-described fluorination or chlorination yields an isomeric mixture, i.e., a mixture of 6β- and 6β-(fluoro or chloro)-D-homosteroids, the mixture can be separated into the pure isomers according to known methods such as chromatography.

The isomerization of a 6β-(fluoro or chloro)-D-homosteroid can be carried out by treatment with an acid, especially a mineral acid such as hydrochloric acid or hydrobromic acid in a solvent (e.g., dioxan or glacial acetic acid).

The methylation of a D-homosteroid of formula III, in accordance with embodiment (d) of the process, can be carried out, for example, by converting a D-homosteroid of formula III into a 3-enol ether (e.g., by treatment with an orthoformic acid ester such as ethyl orthoformate in the presence of an acid such as p-toluenesulphonic acid, if desired with addition of the corresponding alcohol; or by treatment with a dialkoxypropane such as 2,2-dimethoxypropane in methanol/dimethylformamide in the presence of p-toluenesulphonic acid) and reacting the enol ether with a tetrahalomethane (e.g. CBr$_4$, CCl$_2$Br$_2$ or CCl$_3$Br) to give a trihalomethyl-Δ$^4$-3-ketone. A trihalomethyl-Δ$^4$-3-ketone can be dehydrohalogenated with a base such as collidine to give a dihalomethylene-Δ$^4$-3-ketone which can be converted into a 6α-methyl-Δ$^4$-3-ketone by catalytic hydrogenation under mild conditions (e.g., using a Pd/SrCO$_3$ catalyst).

Another methylation procedure consists in converting a 1,2-saturated D-homosteroid of formula III into a 3-enol ether, as described earlier, and reacting this 3- enol ether in a manner known per se to give a corresponding 6-formyl derivative, reducing the formyl group with sodium borohydride to the hydroxymethyl group and finally dehydrating the product with cleavage of the enol ether, there being obtained a 6-methylene-D-homosteroid of the general formula

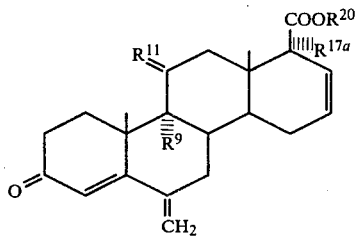

Formula XIII wherein $R^9$, $R^{11}$, $R^{17a}$ and $R^{20}$ have the significance given earlier.

6-methylene-D-homosteroids of formula XIII can also be prepared by converting a D-homosteroid of formula III into a 3-enamine (e.g., the 3-pyrrolidinium enamine), hydroxymethylating the 3-enamine with formaldehyde and cleaving water from the hydroxymethylation product using an acid such as p-toluenesulphonic acid.

A 6-methylene-D-homosteroid of formula XIII can be catalytically hydrogenated to give a corresponding 6-methyl-D-homosteroid of formula I in a manner known per se; for example, using a known hydrogenation catalyst.

The $HR^5$-cleavage from a D-homosteroid of formula IV, in accordance with embodiment (e) of the process, namely a dehydration or a dehydrohalogenation, can be carried out in a manner known per se. The dehydration can be carried out by treatment with an acid (e.g., a mineral acid such as hydrochloric acid) or with a base. The dehydrohalogenation can be carried out using a base (e.g., an organic base such as pyridine).

In carrying out embodiments (f) and (g) of the process, a D-homosteroid of formula V or VI is conveniently dissolved in a suitable solvent (e.g., an ether such as tetrahydrofuran or dioxan, a chlorinated hydrocarbon such as methylene chloride or chloroform or a ketone such as acetone) and left to react with the reagent added thereto. Hypochlorous or hypobromous acid is conveniently itself generated in the reaction mixture; for example, from N-bromo or N-chloroamides or imides such as N-chlorosuccinimide or N-bromoacetamide, and a strong acid, preferably perchloric acid. Embodiment (g) is preferred for the manufacture of 9-fluoro-11-hydroxy-D-homosteroids of formula I.

The hydroxylation of a D-homosteroid of formula VII, in accordance with embodiment (h) of the process, can be carried out according to methods known per se for the microbiological 11-hydroxylation of steroids. For this 11-hydroxylation, there can be used microorganisms of the taxonomic groups Fungi and Schizomycetes, especially of the subgroups Ascomycetes, Phycomycetes, Basidiomycetes and Actinomycetales. There can also be used mutants produced in a chemical manner (e.g., by treatment with nitrite) or in a physical manner (e.g., by irradiation) as well as cell-free enzyme preparations obtained from the microorganisms. Especially-suitable microorganisms for the 11β-hydroxylation are those of the genera Curvularia (e.g., C. lunata NRRL 2380 and NRRL 2178; ATCC 13633, 13432, 14678, IMJ 77007, IFO 2811), Absidia (e.g. A. coerula IFO 4435), Colletotrichum (e.g. C. pisi ATCC 12520), Pellicularia (e.g. P. filamentosa IFO 6675), Streptomyces (e.g. S. fradiae ATCC 10745), Cunninghamella (e.g. C. bainieri ATCC 9244, C. verticillata ATCC 8983, C. elegans NRRL 1392 and ATCC 9245, C. blakesleeana ATCC 8688, 8688a, 8688b, 8983 and C. echinulata ATCC 8984), Pycnosporium (e.g. sp. ATCC 12231), Verticillium (e.g. V. theobromae CBS 39858), Aspergillus (e.g. A. quadrilineatus IAM 2763), Trichothecium (e.g. T. roseum ATCC 12519) and Phoma (e.g. sp. ATCC 13145).

In carrying out embodiment (i) of the process, the keto group in the 3-position of a D-homosteroid of formula VIII is firstly protected. The 3-keto group can be protected by ketalization or, where a 1,2-double bond is present, by formation of an enamine. This protecting group can subsequently be removed by acid hydrolysis. A $\Delta^{1,4}$-3-ketone can be converted into a $\Delta^{1,3,5}$-3-enamine using a secondary amine in the presence of titanium tetrachloride. The reduction of the 11-keto group of a thus-protected D-homosteroid can be carried out using a complex metal hydride such as lithium aluminium hydride, sodium borohydride or diisobutyl aluminium hydride. When the reduction is carried out using sodium borohydride in tetrahydrofuran (Chem. and Ind. 1977, 982), the 11-keto group can be selectively reduced without requiring the intermediate protecting of the $\Delta^{1,4}$-3-keto system.

The oxidation of the 11-hydroxy group in a D-homosteroid of formula IX, in accordance with embodiment (j) of the process, can be carried out using an oxidizing agent such as chromic acid (e.g., $CrO_3$/sulphuric acid in acetone or $CrO_3$/pyridine).

The acylation of a 17a-hydroxy group in a D-homosteroid of formula X, in accordance with embodiment (k) of the process, can be carried out in a manner known per se; for example, by treatment with an acylating agent, such as an acyl chloride or anhydride, in the presence of an acid-binding agent (e.g., pyridine or triethylamine) or in the presence of a strong acid catalyst (e.g., p-toluenesulphonic acid). As the solvent for the acylation, there may be mentioned organic solvents which do not contain hydroxyl groups (e.g., chlorinated hydrocarbons such as methylene chloride or hydrocarbons such as benzene). It is also possible to convert a 17aα-hydroxy-D-homosteroid-17aβ-carboxylic acid of formula X with a corresponding carboxylic acid anhydride initially into a mixed anhydride of the steroid carboxylic acid and to treat this mixed anhydride with an acid or base (e.g., with aqueous acetic acid or aqueous pyridine) to give the desired 17aα-acyloxy-D-homosteroid of formula I.

The functional modification of the group —$COOR^{201}$ in a D-homosteroid of formula XI, in accordance with embodiment (l) of the process, can consist, for example, in an esterification of a 20-carboxyl group, a trans-esterification of an esterified 20-carboxyl group or a halogen-exchange. All of these reactions can be carried out according to methods known per se. The esterification can be carried out, for example, by treating the free acid with a diazoalkane (e.g., diazomethane in ether) or with an O-alkyl-N,N'-dicyclohexylisourea in an aprotic solvent or by reacting a salt of the acid (e.g., an alkali metal salt) with an alkyl halide or sulphate (e.g., methyl or ethyl iodide or dimethyl or diethyl sulphate).

The trans-esterification of an esterified carboxyl group (e.g., the replacement of an alkyl group denoted by $R^{201}$ by another alkyl group) can be carried out by reaction with the corresponding alcohol in the presence of an acid catalyst such as perchloric acid. D-homosteroids in which $R^{201}$ represents a halo-(lower alkyl) group can be manufactured, for example, by reacting a salt of a D-homosteroid carboxylic acid of formula XI with a dihaloalkane such as, for example, chloroiodomethane or methylene chloride or with a sulphonyloxyalkyl halide to give a sulphonyloxyalkyl ester and treating the latter with an alkali metal or alkaline earth metal halide (e.g., lithium chloride in dimethylformamide) in order to obtain a halo-(lower alkyl) substituent $R^{201}$. Halo-(lower alkyl) esters can also be obtained by reacting a D-homosteroid carboxylic acid with an appropriate aldehyde in the presence of a hydrogen halide, conveniently in the presence of a catalyst such as zinc chloride.

The hydrogenation of a 1,2-double bond in a D-homosteroid of formula XII, in accordance with embodiment (m) of the process, can be carried out catalytically; for example, using palladium or tris(triphenylphosphine)rhodium chloride.

The starting materials used in the foregoing process, insofar as they are not known or insofar as their preparation is not described hereinafter, can be prepared in analogy to known methods or methods described in the examples hereinafter.

The D-homosteroids of formula I possess endocrinal, especially antiinflammatory, activity. They show a good ratio of the antiinflammatory activity to effects of a mineralo or glucocorticoidal nature.

In Table I, there are compiled the results obtained with two D-homosteroids of formula I in two standard tests which demonstrate the activities of the class of compounds. The tests carried out can be described as follows:

1. Mouse Ear Test

The D-homosteroids, dissolved in croton oil, were applied for 15 seconds under a pressure of 600 g to the right ear of male mice weighing 25-30 g. The left ear served as the control. Four hours later, the mice were killed, and tissue was removed with a punch from the same position on treated and untreated ears and weighed. The $EC_{50}$, namely that concentration which gave a 50% oedema inhibition in comparison with a control group, was determined.

2. Felt Pellet Test

Two felt pellets were implanted under the skin (scapula region) in female rats (90-110 g) under ether narcosis. The D-homosteroids were administered orally on four successive days commencing on the day of the implantation. On the 5th day, the rats were killed, and the granulomas which formed were removed, dried and weighed. The $ED_{40}$, namely that dosage which gave a 40% reduction of the granulation weight, was determined.

TABLE I

| D-Homosteriod | Mouse Ear Test $EC_{50}$ (mg/ml) | Felt Pellet $ED_{40}$ (mg/kg) |
|---|---|---|
| 17aα-Acetoxy-11-hydroxy-3-oxo-D-homoandrosta-1,4,16-trieno-17β-carboxylic acid methyl ester | 0.03 | 6.4 |
| 17aα-Acetoxy-9-fluoro-11-hydroxy-3-oxo-D-homoandrosta-1,4,16-triene-17β-carboxylic acid methyl ester | 0.01 | 6.0 |

The D-homosteroids of formula I can be used as medicaments in the form of pharmaceutical preparations having direct or delayed liberation of the active ingredient in association with a compatible pharmaceutical carrier material. This carrier material can be an organic or inorganic inert carrier material suitable for enteral, percutaneous or parenteral application such as, for example, water, gelatin, gum arabic, lactose, starch, magnesium stearate, talc, vegetable oils, polyalkyleneglycols, petroleum jelly, etc. The pharmaceutical preparations can be made up in a solid form (e.g., as tablets, dragees, suppositories, or capsules), in a semi-solid form (e.g., as salves) or in a liquid form (e.g., as solutions, suspensions or emulsions). The pharmaceutical preparations may be sterilized and/or may contain adjuvant substances such as preserving, stabilizing, wetting or emulsifying agents, salts for the variation of the osmotic pressure or buffer substances.

In general, the dosage range in the case of pharmaceutical preparations for topical administration can be about 0.01-1% of a D-homosteroid of formula I. In the case of pharmaceutical preparations for systemic administration, about 0.1-10 mg of a D-homosteroid of formula I can be provided per administration.

The pharamaceutical preparations can be prepared in a manner known per se by mixing a D-homosteroid of formula I with nontoxic solid and/or liquid carrier materials which are customary in pharmaceutical preparations and which are suitable for therapeutic administration (e.g., the carrier materials mentioned earlier) and, if desired, transforming the mixture into the desired pharmaceutical dosage form.

The following examples illustrate the process provided by the present invention:

EXAMPLE 1

A 2 liter Erlenmeyer flask containing 500 ml of a nutrient solution, sterilized for 30 minutes at 120° C. in an autoclave, consisting of 6% liquid starch sugar (3% glucose), 1% cornsteep, 0.2% $NaNO_3$, 0.1% $KH_2PO_4$, 0.2% $K_2HPO_4$, 0.05% $MgSO_4$, 0.002% $FeSO_4$, 0.05% KCl, adjusted to pH 6.0, is inoculated with a lyophilized culture of Phoma sp. ATCC 13145 and shaken at 30° C. for 72 hours. This pre-culture is used to inoculate a 20 liter stainless steel fermenter containing 15 liters of a medium of the same composition sterilizsed at 121° C. and 1.1 atmospheres. An anti-foam agent is added, and germination is carried out for 24 hours at 29° C. with aeration (15 liters/minute), at 0.7 atmosphere pressure and while stirring (220 revolutions per minute). One liter of the culture broth is transferred under sterile conditions into 14 liters of a medium of the same composition, sterilized as described earlier and cultivated under the same conditions. After 12 hours, a solution filtered sterile, of 3 g of 17aα-acetoxy-3-oxo-D-homo-4,16-androstadiene-17aβ-carboxylic acid methyl ester in 100 ml of dimethylformamide is added. After a contact time of 53 hours, the content of the fermenter is filtered over gauze, and the filtrate is stirred twice with 10 liters of methyl isobutyl ketone each time. The filtered-off mycelium is also washed with methyl isobutyl ketone. The wash solutions and extracts are combined and evaporated in vacuo at 50° C. (bath temperature). In order to remove the anti-foam agent, the residue is washed several times with hexane and recrystallized from ethyl acetate with the addition of carbon. From three combined fermenter batches with a total substrate charge of 8.8 g, there are obtained 2.79 g of 17aα-acetoxy-11β-hydroxy-3-oxo-D-homoandrosta-4,16-diene-17aβ-carboxylic acid methyl ester of melting point 228°/229°–231° C. By chromatography of the mother liquors, there are obtained a further 1.32 g of the desired product. The total yield is 44.9% of theory.

EXAMPLE 2

A 2 liter Erlenmeyer flask containing 500 ml of a nutrient solution, sterilized for 30 minutes at 120° C. in an autoclave, consisting of 1.5% peptone, 1.2% cornsteep and 0.2% MgSO$_4$, adjusted to pH 6.5, is inoculated with a lyophilized culture of Bacillus lentus (ATCC 13805) and shaken for 24 hours at 30° C. This pre-culture is used to inoculate a 20 liter stainless steel fermenter containing 15 liters of a liquid nutrient medium, sterilized at 121° C. and 1.1 atmospheres, consisting of 0.1% peptone, 0.2% cornsteep, 0.5% glucose and 0.2% yeast extract, adjusted to pH 7.0. After 24 hours, 0.9 liters of the culture are transferred under sterile conditions into a similar-sized fermenter which has been charged with 14 liters of the same nutrient solution and sterilized. An anti-foam agent is added, and germination is carried out at 29° C. with aeration and stirring. After a growth phase of 6 hours, a solution, filtered sterile, of 1.5 g of 17aα-acetoxy-11β-hydroxy-3-oxo-D-homoandrosta-4,16-diene-17aβ-carboxylic acid methyl ester in 50 ml of dimethylformamide is added. After a contact time of 32 hours, the content of the fermenter is extracted twice with 10 liters of methyl isobutyl ketone each time, and the extract is evaporated in vacuo. In order to remove the anti-foam agent, the residue is washed with hexane and recrystallized from ethyl acetate. From three fermenter batches with a total substrate charge of 4.2 g, there are obtained, including fractions obtained by mother liquor chromatography, 2.4 g of 17aα-acetoxy-11β-hydroxy-3-oxo-D-homoandrosta-1,4,16-triene-17aβ-carboxylic acid methyl ester of melting point 236°/237°–239° C. (57.5% of theory).

EXAMPLE 3

1.12 g of 17a-acetoxy-3-oxo-D-homoandrosta-1,4,9(11),16-tetraene-17aβ-carboxylic acid methyl ester in 38 ml of dioxan were treated with 7.7 ml of water, 0.58 g of N-bromoacetamide and 3.85 ml of 10% perchloric acid, and the mixture was stirred at 25° C. for 30 minutes. After the addition of 2 g of sodium sulphite, the solvent was evaporated off in vacuo. The residue, in methylene chloride, was washed with water and dilute sodium chloride solution. The methylene chloride solution was dried and evaporated in vacuo. From acetone/hexane, there was obtained 17a-acetoxy-9-bromo-11β-hydroxy-3-oxo-D-homoandrosta-1,4,16-triene-17aβ-carboxylic acid methyl ester of melting point 213° C.; $[\alpha]_D = -50°$ (c=0.1% in dioxan); UV: $\epsilon_{242} = 14540$.

The starting material is obtained from 17a-acetoxy-11β-hydroxy-3-oxo-D-homoandrosta-1,4,16-triene-17aβ-carboxylic acid methyl ester by treatment with methanesulphonyl chloride and sulphur dioxide in pyridine and dimethylformamide.

EXAMPLE 4

953 mg of 17a-acetoxy-9,11β-epoxy-3-oxo-D-homo-9β-androsta-1,4,16-triene-17aβ-carboxylic acid methyl ester were stirred at 30° C. for 5.5 hours in 4.3 ml of toluene and 2.9 ml of pyridine 0.5 HF. The mixture was diluted with methylene chloride, washed neutral with water, dilute sodium bicarbonate solution and dilute sodium chloride solution, dried and evaporated in vacuo. After chromatography on silica gel, there was obtained from acetone/hexane 17-acetoxy-9-fluoro-11β-hydroxy-3-oxo-D-homoandrosta-1,4,16-triene-17aβ-carboxylic acid methyl ester of melting point 257° C.; $[\alpha]_D = -114°$ (c=0.1% in dioxan); UV: $\epsilon_{239} = 15400$.

The starting material is obtained from 17a-acetoxy-9-bromo-11β-hydroxy-3-oxo-D-homoandrosta-1,4,16-triene-17aβ-carboxylic acid methyl ester and potassium carbonate in acetone at reflux.

EXAMPLE 5

In a manner analogous to that described in Example 3, from 17a-acetoxy-3-oxo-D-homoandrosta-4,9(11),16-triene-17aβ-carboxylic acid methyl ester [melting point 201°–202° C.; $[\alpha]_D = -152°$ (c=0.1% in dioxan); UV: $\epsilon_{238} = 17890$], there is obtained 17a-acetoxy-9-bromo-11β-hydroxy-3-oxo-D-homoandrosta-4,16-diene-17aβ-carboxylic acid methyl ester of melting point 154°–155° C.; $[\alpha]_D = -39°$ (c=0.1% in dioxan); UV: $\epsilon_{243} = 15530$.

EXAMPLE 6

In a manner analogous to that described in Example 4, from 17a-acetoxy-9,11β-epoxy-3-oxo-D-homo-9β-androsta-4,16-diene-17aβ-carboxylic acid methyl ester [melting point 213°–214° C.; $[\alpha]_D = -201°$ (c=0.1% in dioxan); UV: $\epsilon_{241} = 15400$], there is obtained 17a-acetoxy-9-fluoro-11β-hydroxy-3-oxo-D-homoandrosta-4,16-diene-17aβ-carboxylic acid methyl ester of melting point 192°–193° C.; $[\alpha]_D = -100°$ (c=0.1% in dioxan); UV: $\epsilon_{238} = 17060$.

EXAMPLE 7

450 mg of 9-fluoro-11β-hydroxy-3-oxo-17a-propionyloxy-D-homoandrosta-4,16-diene-17aβ-carboxylic acid and 450 mg of sodium hydrogen carbonate were boiled at reflux at 60° C. for 20 hours in 34 ml of dimethylacetamide and 115 ml of methylene chloride. The mixture was filtered, and the filtrate was evaporated in vacuo. The residue was taken up in methylene chloride and washed with water. The methylene chloride solution was dried and evaporated in vacuo. Chromatography of the crude product on silica gel gave 206 mg of 9-fluoro-11β-hydroxy-3-oxo-17a-propionyloxy-D-homoandrosta-4,16-diene-17aβ-carboxylic acid chloromethyl ester of melting point 176°–177° C.; $[\alpha]_D = -56°$ (c=0.1% in dioxan); UV: $\epsilon_{238} = 14540$.

The starting material can be prepared as follows:

Treatment of 17a-acetoxy-9-fluoro-11β-hydroxy-3-oxo-D-homoandrosta-4,16-diene-17aβ-carboxylic acid methyl ester with potassium hydroxide in methoxyethanol yields 9-fluoro-11β,17a-dihydroxy-3-oxo-D-homoandrosta-4,16-diene-17aβ-carboxylic acid of melting point 222°–224° C. By reaction of this acid with propionyl chloride in dichloromethane in the presence of triethylamine, there is obtained 9-fluoro-11β-hydroxy-3-oxo-17a-propionyloxy-D-homoandrosta-4,16-diene-4,16-diene-17aβ-carboxylic acid.

EXAMPLE 8

In a manner analogous to that described in Example 7, from 11β-hydroxy-3-oxo-17a-propionyloxy-D-homoandrosta-4,16-diene-17aβ-carboxylic acid, there is obtained 11β-hydroxy-3-oxo-17a-propionyloxy-D-homoandrosta-4,16-diene-17aβ-carboxylic acid chloromethyl ester of melting point 192°–193° C.; $[\alpha]_D = -34°$ (c=0.1% in dioxan); UV: $\epsilon_{241} = 15290$.

EXAMPLE 9

680 mg of 11β-hydroxy-3-oxo-17a-propionyloxy-D-homoandrosta-4,16-diene-17aβ-carboxylic acid chloromethyl ester and 1.36 g of silver fluoride were stirred at 50° C. for 40 hours in 8.5 ml of acetonitrile. After the addition of 50 ml of ethyl acetate, the mixture was filtered, washed with water and sodium chloride solution, dried and evaporated. From ether, there crystallized 297 mg of 11β-hydroxy-3-oxo-17a-propionyloxy-D-homoandrosta-4,16-diene-17aβ-carboxylic acid fluoromethyl ester of melting point 150°–151° C.; $[\alpha]_D = -71°$ (c=0.1% in dioxan); UV: $\epsilon_{240} = 15940$.

EXAMPLE 10

500 mg of 17a-acetoxy-11β-hydroxy-3-oxo-D-homoandrosta-4,16-diene-17aβ-carboxylic acid methyl ester were dissolved in 5 ml of hot ethanol and, after cooling to 25° C., treated with 5 ml of triethyl orthoformate and 5 mg of p-toluenesulphonic acid. 0.05 ml of pyridine was added after 15 minutes. The mixture was diluted with methylene chloride, washed with water, dried and evaoporated. The resulting crude 17a-acetoxy-3-ethoxy-11β-hydroxy-D-homoandrosta-3,5,16-triene-17aβ-carboxylic acid methyl ester was treated at 0° C. in 30 ml of acetone with 240 mg of N-chlorosuccinimide and a solution of 300 mg of sodium acetate and 0.28 ml of acetic acid in 6 ml of water. After 30 minutes, the acetone was removed by evaporation in vacuo, the residue was taken up in methylene chloride and washed with sodium hydrogen carbonate solution and sodium chloride solution. Evaporation of the dried methylene chloride solution gave a mixture of the epimers of 17a-acetoxy-6-chloro-11β-hydroxy-3-oxo-D-homoandrosta-4,16-diene-17aβ-carboxylic acid methyl ester. This was left to stand at 25° C. in 25 ml of acetic acid and 5 ml of 25% hydrochloric acid. After 4 hours, the solvent was removed by evaporation in vacuo. Purification of the residue on silica gel gave 17a-acetoxy-6α-chloro-11β-hydroxy-3-oxo-D-homoandrosta-4,16-diene-17aβ-carboxylic acid methyl ester.

EXAMPLE 11

Treatment of 17a-acetoxy-11β-hydroxy-3-oxo-D-homoandrosta-4,16-diene-17aβ-carboxylic acid methyl ester with pyrrolidine in methanol yields 17a-acetoxy-11β-hydroxy-3-(1-pyrrolidinyl)-D-homoandrosta-3,5,16-triene-17aβ-carboxylic acid methyl ester. Treatment of this enamine with formalin solution in methanol and benzene yields 17a-acetoxy-11β-hydroxy-6-hydroxymethyl-3-oxo-D-homoandrosta-4,16-diene-17aβ-carboxylic acid methyl ester. Treatment of this ester with hydrochloric acid in dioxan yields 17a-acetoxy-11β-hydroxy-6-methylene-3-oxo-D-homoandrosta-4,16-diene-17aβ-carboxylic acid methyl ester. 580 mg of 17a-acetoxy-11β-hydroxy-6-methylene-3-oxo-D-homoandrosta-4,16-diene-17aβ-carboxylic acid methyl ester and 290 mg of 5% palladium/carbon were boiled at reflux in 3 ml of cyclohexene and 30 ml of ethanol until the UV spectrum of a removed sample no longer showed absorption in the range of 290–300 nm. The mixture was filtered, treated with 15 ml of 25% hydrochloric acid and left to stand for 1 hour. After evaporation of the solvent and purification of the residue on silica gel, there was obtained 17a-acetoxy-11β-hydroxy-6α-methyl-3-oxo-D-homoandrosta-4,16-diene-17aβ-carboxylic acid methyl ester.

EXAMPLE 12

110 mg of 17a-acetoxy-5α-bromo-6β-fluoro-11β-hydroxy-3-oxo-D-homoandrosta-16-ene-17aβ-carboxylic acid methyl ester in 1 ml of glacial acetic acid were stirred at 25° C. for 2 hours with 0.02 ml of 33% hydrogen bromide in glacial acetic acid. The mixture was diluted with ethyl acetate, washed with water, sodium hydrogen carbonate solution and dilute sodium chloride solution, dried and evaporated. Purification of the crude product on silica gel gave 17a-acetoxy-6α-fluoro-11β-hydroxy-3-oxo-D-homoandrosta-4,16-diene-17aβ-carboxylic acid methyl ester.

EXAMPLE 13

275 mg of 17a-acetoxy-11β-hydroxy-3-oxo-D-homoandrosta-1,4,16-triene-17aβ-carboxylic acid methyl ester in 15 ml of acetone were treated with 0.25 ml of Jones reagent (26.72 g of $CrO_3$, 23 ml of concentrated sulphuric acid, water up to a total volume of 100 ml), and the mixture was stirred at 25° C. After 15 minutes, the mixture was treated with 100 ml of water and extracted three times with 30 ml of methylene chloride. The organic phases were washed once with dilute sodium hydrogen carbonate solution and once with saturated sodium chloride solution and then dried with sodium sulphate. After removal of the solvent in vacuo, there were obtained 260 mg of 17a-acetoxy-3,11-dioxo-D-homoandrosta-1,4,16-triene-17aβ-carboxylic acid methyl ester.

EXAMPLE 14

400 mg of 17a-hydroxy-3,11-dioxo-D-homoandrosta-1,4,16-triene-17aβ-carboxylic acid methyl ester, 1 ml of acetic acid anhydride and 1.6 g of dimethtylaminopyridine were boiled at reflux for 36 hours in 20 ml of benzene. The mixture was diluted with ether and water. The ether phase was washed with dilute hydrochloric acid, dilute sodium hydrogen carbonate solution and saturated sodium chloride solution, dried and evaporated in vacuo. Chromatography of the residue on silica gel gave 17a-acetoxy-3,11-dioxo-D-homoandrosta-1,4,16-triene-17aβ-carboxylic acid methyl ester.

EXAMPLE 15

600 mg of 17a-acetoxy-3β,11β-dihydroxy-D-homoandrosta-5,16-diene-17aβ-carboxylic acid methyl ester and 800 mg of aluminium tert. butylate were boiled at reflux in 8 ml of acetone and 20 ml of benzene. After 8 hours, the mixture was diluted with ethyl acetate, washed with dilute hydrochloric acid and water, dried and evaporated in vacuo. Purification of the residue on silica gel gave 17a-acetoxy-11β-hydroxy-3-oxo-D-homoandrosta-4,16-diene-17aβ-carboxylic acid methyl ester, m.p. 229° C.

EXAMPLE 16

100 mg of 17a-acetoxy-3,11-dioxo-D-homoandrosta-1,4,16-triene-17aβ-carboxylic acid methyl ester and 30 mg of sodium borohydride were stirred at 30° C. for 5 hours in 3 ml of tetrahydrofuran. The mixture was diluted with water and extracted twice with methylene chloride. The organic solutions were washed with water and saturated sodium chloride solution, dried and evaporated in vacuo. Preparative thin-layer chromatography gave 17a-acetoxy-11β-hydroxy-3-oxo-D-homoandrosta-1,4,16-triene-17aβ-carboxylic acid methyl ester of melting point 237°–238° C.

EXAMPLE 17

300 mg of 17a-acetoxy-11β-hydroxy-3-oxo-D-homoandrosta-1,4,16-triene-17aβ-carboxylic acid methyl ester and 300 mg of tris(triphenylphosphrine)rhodium chloride were dissolved under hydrogen in 7 ml of benzene and 7 ml of ethanol, and the solution was stirred at 25° C. for 30 hours. After evaporation of the solvent in vacuo and chromatography of the residue on silica gel, there was obtained 17a-acetoxy-11β-hydroxy-3-oxo-D-homoandrosta-4,16-diene-17aβ-carboxylic acid methyl ester of melting point 228°–230° C.

The following examples illustrate the preparation of salves containing a D-homosteroid of formula I as the active ingredient:

EXAMPLE A

| Active ingredient | 0.1 wt.% |
| Liquid paraffin | 10.0 wt.% |
| Soft white paraffin q.s. ad | 100.0 parts by weight |

The active ingredient (D-homosteroid) is ground with some of the liquid paraffin in a ball mill until a particle size of less than 5μ is attained. The paste is diluted, and the mill is washed out with the remainder of the liquid paraffin. The suspension is added to the melted colorless white paraffin at 50° C., and the mixture is stirred until it becomes cold, there being obtained a homogeneous salve.

EXAMPLE B

| Active ingredient | 0.25 wt.% |
| Aluminium stearate | 3.20 wt.% |
| Liquid paraffin q.s. ad | 100.00 parts by weight |

The aluminium stearate is dispersed in the liquid paraffin by vortex-stirring. The suspension is heated with further stirring, the temperature increase being carried out at a rate of 2° C. per minute until a temperature of 90° C. is attained. The temperature is held at 90° C. to 95° C. for 30 minutes until a gel is formed. It is then cooled down rapidly. The active ingredient (D-homosteroid) is milled to a particle size of below 5μ, ground thoroughly with a small portion of the gel and finally worked into the remaining portion of the gel, there being thus obtained a homogeneous mixture.

What is claimed is:
1. D-homosteroids of the formula

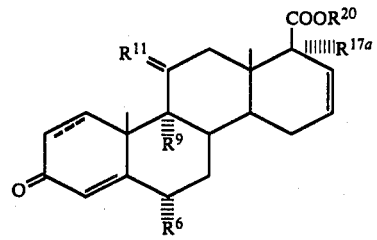

wherein $R^6$ is hydrogen, fluorine, chlorine or methyl; $R^9$ is hydrogen, fluorine, chlorine or bromine; $R^{11}$ is oxo or (α-H,β-OH) when $R^9$ is hydrogen, or $R^{11}$ is oxo, (α-H,β-OH), (α-H,β-fluoro) or (α-H,β-chloro) when $R^9$ is fluorine, chlorine or bromine, with the proviso that, in the case of 9,11-dihalo compounds, the atomic number of the halogen in the 9-position is not less than the atomic number of the halogen in the 11-position; $R^{17a}$ is acyloxy selected from the group consisting of alkanoyloxy containing from 1–7 carbon atoms, undecylenyloxy, oleyloxy, cyclopentylpropionyloxy, cyclohexylpropionyloxy, phenylacetyloxy, salicyloxy, acetylsalicyloxy and benzoyloxy; and $R^{20}$ is lower alkyl or halo-(lower alkyl) and wherein the broken line in the 1,2-position denotes an optional carbon-carbon bond.

2. The D-homosteroid of claim 1 wherein $R^{11}$ is (α-H,β-OH).

3. The D-homosteroid of claim 1 wherein $R^9$ is hydrogen or fluorine.

4. The D-homosteroid of claim 1 wherein $R^{17a}$ is alkanoyloxy containing from 1 to 7 carbon atoms and $R^{20}$ is methyl or fluoromethyl.

5. The D-homosteroid of claim 1 which is 17aα-acetoxy-11β-hydroxy-3-oxo-D-homoandrosta-1,4,16-triene-17β-carboxylic acid methyl ester.

6. The D-homosteroid of claim 1 which is 17aα-acetoxy-9-fluoro-11β-hydroxy-3-oxo-D-homoandrosta-1,4,16-triene-17β-carboxylic acid methyl ester.

7. The D-homosteroid of claim 1 which is 11β-hydroxy-3-oxo-17a-propionyloxy-D-homoandrosta-4,16-diene-17aβ-carboxylic acid fluoromethyl ester.

* * * * *